United States Patent [19]

Dozzi et al.

[11] 4,258,226

[45] Mar. 24, 1981

[54] AROMATIC HYDROGENATION

[75] Inventors: Giovanni Dozzi, Milan; Salvatore Cucinella, San Donato Milanese, both of Italy

[73] Assignee: Anic, S.p.A., Palermo, Italy

[21] Appl. No.: 103,489

[22] Filed: Dec. 14, 1979

Related U.S. Application Data

[62] Division of Ser. No. 921,002, Jun. 30, 1978, Pat. No. 4,217,246.

[30] Foreign Application Priority Data

Jul. 27, 1977 [IT] Italy .................................. 26190 A/77

[51] Int. Cl.$^3$ ........................... C07C 5/02; C07C 5/10
[52] U.S. Cl. ................................ 585/270; 252/429 B; 252/429 R
[58] Field of Search .................... 585/270; 252/429 R, 252/429 B

[56] References Cited

U.S. PATENT DOCUMENTS

| | | | |
|---|---|---|---|
| 3,068,180 | 12/1962 | Van Amoronzin | 252/429 B |
| 3,238,265 | 3/1966 | Mueller | 252/429 B |
| 3,511,891 | 5/1970 | Taylor et al. | 252/429 B |
| 3,558,736 | 1/1971 | Bergen et al. | 252/429 B |

*Primary Examiner*—Veronica O'Keefe
*Attorney, Agent, or Firm*—Morgan, Finnegan, Pine, Foley & Lee

[57] ABSTRACT

For hydrogenating unsaturated compounds, and especially those containing aromatic rings, a catalytic system of novel conception is suggested. This is a quaternary heterogeneous system which comprises an elemental metal of Groups IIA or IIIA, a primary or a secondary amine, a Ni or a Co halide, and an activator such as Na, NaH, NaAlH$_4$ or AlEt$_3$.

Very satisfactory results as to yields and smoothness of reaction are obtained in the conversion of benzene to cyclohexane and of toluene to methylcyclohexane.

19 Claims, No Drawings

AROMATIC HYDROGENATION

This is a division of application Ser. No. 921,002 filed June 30, 1978; now U.S. Pat. No. 4,217,246.

This invention relates to a novel method for the hydrogenation of unsaturated compounds and, more particularly, or aromatic rings.

It is known, from the prior art literature, that it is possible to hydrogenate aromatic rings under comparatively bland conditions as to temperature and pressure, either in a homogeneous or heterogenous phase by adopting catalytic systems based, for example, on Pt, Pd, Rh, Ir, Ru, that is very expensive metals, such catalysts being easily prone to being poisoned and to originate regeneration problems.

In order that satisfactory conversions may be obtained, a high ratio of catalyst to substrate is often required (see for ex. Practical Catalytic Hydrogenation by Morris Freigelder, Wiley Interscience, 1971, and Catalytic Hydrogenation, by R. Augustine, M. Dekker, Inc. New York, 1965).

It is likewise known that the hydrogenation of aromatic rings can take place under drastic temperatures and pressures by using heterogeneous catalytic systems such as Ni-Raney or Co-Raney (H. A. Smith, The Catalytic Hydrogenation of aromatic compounds, Catalysis V, 175 (1957).

These catalysts, however, are impaired by considerable shortcomings for the following reasons:

(a) They must be used as they are formed, since their activity is decreased with the lapse of time;

(b) They must be employed in comparatively high amounts as compared with the quantity of the substrate to be hydrogenated;

(c) Their preparation is such as to require a lengthy and intricate run which contemplates also high-temperature steps (B. W. Aller, J. Appl. Chem., 7, 130 (1957), Ibid. 8, 163 (1958), and Ibid. 8, 492, (1958)). Moreover, at the high temperatures at which they are employed, such catalyst may either become inactivated or they may start cleavage reactions of the —C—C— bonds ("Catalytic behaviour of Cobalt-Cobalt, its chemistry, metallurgy and uses", by M. F. L. Johnson, Am. Chem. Soc. Reinhold Publishing Corp., New York, 1960).

Catalysts of the kinds referred to above must be finely dispersed on specially provided supporting members. It should also be recalled that the use of certain solvents, such as alcohols, with catalysts based on noble metals or Ni-Raney or Co-Raney, especially if they are supported, is a hazard since these catalysts are also oxidizing catalysts and can set fire on the solvent vapors.

We have now ascertained and this is the subject matter of the present invention, that a method for the hydrogenation of unsaturated compounds, more particularly aromatic rings, can be used with advantage, such method being characterized in that it employs a catalytic system formed by the product of the reaction among the following compounds:

(a) a metal of the Group IIA, or IIIA, as defined by the classification reported in the Handbook of Chemistry and Physics, Chemical Rubber Publishing Co. 39th Edition;

(b) a primary or a secondary amine;

(c) a halide selected from the group consisting of the halides of Co, Ni; and (d) an activating substance selected from the group consisting of Na, NaH, NaAlH$_4$, Al Et$_3$ and others.

Generally speaking, the molar ratio of the component (a) to the component (b) is stoichiometric, otherwise a slight excess of (b) is adopted, for example up to 20%. The molar ratio of the component (a) to component (c) can be varied from 0.1 to 100, the range from 4 to 8 being preferred.

The quantity of the activator (i.e. component (d)) is smaller than, or equal to, 5% molar percent relative to the componend (a). The molar ratio of the Nickel (or Cobalt) compound to the substrate to be hydrogenated can be equal to, or higher than, 1:10$^6$, and the preferred range is from 1:10$^3$ to 1:10$^4$.

The hydrogenation temperature can be varied according to the product to be hydrogenated, from room temperature to the decomposition temperature of the product concerned, temperatures from 100° C. to 200° C. being preferred.

Also the hydrogen pressure can be varied within a wide range, from the atmospherical pressure to 1,000 kg/cm$^2$, the interval from atmospherical pressure to 150 kg/cm$^2$ being preferred.

Preferred examples of the component (a) are Al, Mg, B.

Examples of the component (b) are primary or secondary amines, aliphatic or cycloaliphatic in character: methylamine, ethylamine, nor. propylamine, nor. butylamine, isopropylamine, sec. butylamine, tert. butylamine, cyclohexylamine, dimethylamine and others.

Examples of the component (c) are CoCl$_2$, NiCl$_2$, and other halides and/or complexes thereof with Lewis' bases.

Examples of the component (d) are those reported above.

The catalyst of this invention is heterogeneous in character and, if stored in an inert atmosphere, it keeps its activity in time and can thus be employed as such in consecutive hydrogenation runs.

Summing up, the catalyst of the present invention affords a number of advantages: it does not require any cumbersome preparation, it is very active also when it is not supported, it can be employed repeatedly, it is not pyrophoric, it does not give rise to any side reactions of cracking or —C—C— bond cleavage, no solvent being required since the substrate itself, to be hydrogenated, can act as the reaction solvent.

The several components of the catalytic system can discretely be introduced in the autoclave together with the substrate to be hydrogenated. The catalytically active system is thus formed "in situ". After having charged the autoclave with a quantity of hydrogen which is equal to, or slightly higher than, the amount required for the hydrogenation of the aromatic compound concerned, the hydrogen main can be cut off during the entire reaction time.

The progress of the hydrogenation reaction can thus be monitored by checking the gradual decrease of the pressure indicated by the pressure gauge and when the hydrogenation proceeds in a complete manner, no more hydrogen pressure is seen in the autoclave, this being in agreement with the fact that the hydrogenation reaction of unsaturated compounds, and more particularly of aromatic rings, proceeds, with the catalyst system in question also under a pressure which is equal to the ambient pressure or even below same.

In order that the present invention may be thoroughly illustrated, a few exemplary embodiments are given, which are no limitations.

EXAMPLE I

A one-liter stainless steel autoclave (the hydrogen-feed system connected to the autoclave causes the overall volume of the latter to be from 1.3 liter to 1.4 liter) equipped with an electric heating system, anchor-shaped magnetic stirrer, is previously evacuated of air and charged with a slurry of powdered aluminium (200 millimols), $CoCl_2$ (30 millimols), $NaAlH_4$ (10 millimols), isopropylamine (230 millimols) in an overall volume of 600 mls of benzene.

The autoclave is pressurized with hydrogen to about 145 kg/cm$^2$ of hydrogen and, after having cut off the hydrogen main, is heated to 160° C. and thus an initial pressure increase is experienced, the autoclave being allowed to stand at this temperature for 8 hours, with stirring.

The hydrogen is thoroughly absorbed. After cooling, the autoclave is pressurized with hydrogen again and the hydrogenation reaction is continued under the same conditions as before: after a time of 6 hrs. approx. no more pressure of hydrogen in the autoclave is found. The autoclave is now pressurized with hydrogen again, that is for the third time and, working still under the same conditions as before, the autoclave is cooled after about 6 hrs. and no pressure is indicated by the gauge any more.

The gaschromatographic analysis of the solution drawn from the autoclave upon decantation, indicates an 88% conversion of the benzene charge to cyclohexane.

EXAMPLE 2

By adopting the same procedure as in Example 1, the autoclave is charged with a slurry of powdered aluminium (200 millimols). $NiCl_2$ (30 millimols), $NaAlH_4$ (10 millimols), isopropylamine (230 millimols) in an overall volume of 250 mls toluene.

The autoclave is pressurized with hydrogen at 140 kg/cm$^2$ and, after having cut off the hydrogen main, is heated to 160° C. and the result is an initial pressure increase, whereafter the autoclave is allowed to stand at this temperature for about 8 hrs., with stirring.

Upon cooling, the residual pressure was about 20 kg./sq.cm and the autoclave was restored to ambient pressure and the gaschromatographic analysis carried out on the solution upon decantation shows an 87% conversion of toluene to methylcyclohexane. After having drawn the methylcyclohexane, 300 mls toluene are introduced in the autoclave and, operating under the same conditions as to temperature, pressure and reaction time as before, a 76% conversion to methylcyclohexane is ascertained.

EXAMPLE 3

The autoclave is charged with the slurry composed by powdered aluminium (130 millimols), $CoCl_2$ (30 millimols), aluminium triethyl (7 millimols), isopropylamine (120 millimols) in an overall volume of 300 mls of toluene.

The autoclave is pressurized with hydrogen at 130 kg/cm$^2$ whereafter it is heated to 170° C. and the result is an initial pressure increase. The autoclave is allowed to stand at this temperature for 8 hrs. with stirring. The autoclave is then cooled, the residual pressure of hydrogen is now 60 kg/cm$^2$. The pressure is released and, on the solution, drawn upon decantation, the gaschromatographic analysis indicates a 36% conversion of toluene to methylcyclohexane.

EXAMPLE 4

By operating under the same conditions as in Example 3, but using powdered magnesium (150 millimols), $CoCl_2$ (30 millimols), $NaAlH_4$, (8 millimols), isopropylamine (150 millimols), a conversion of toluene to methylcyclohexane of 35% has been observed.

EXAMPLE 5

A slurry composed by powdered aluminium (200 millimols), $CoCl_2$ (30 millimols), $NaAlH_4$ (10 millimols), and isopropylamine (230 millimols) in an overall volume of 250 mls of toluene is introduced in the autoclave as used in the previous examples. The hydrogen pressure is brought to 145 kg/cm$^2$ and the autoclave is heated to 170° C., the result being an initial pressure increase. The autoclave is allowed to stand under such conditions for 8 hrs. approx., whereafter the autoclave, when cooled to ambient temperature, is no longer under pressure and indicates a complete absorption of the initially introduced hydrogen. The gaschromatographic analysis carried out on the solution obtained upon decantation of the slurry drawn from, the autoclave, has confirmed the complete hydrogenation of the toluene to methylcyclohexane.

50 mls of the slurry, stored during 20 days under nitrogen, are added to 300 mls of toluene and introduced in the autoclave, operating under the same conditions of temperature, hydrogen pressure and reaction time as specified hereinabove, whereafter a 40% conversion of toluene to methylcyclohexane is observed.

EXAMPLE 6

A slurry composed by powdered aluminium (200 millimols), $NiCl_2$ (30 millimols), $NaAlH_4$ (10 millimols), and isopropylamine (230 millimols) in an overall volume of 300 mls of benzene is introduced in the autoclave. The hydrogen pressure is brought to 145 kg/cm$^2$ and the temperature is raised to 170° C., an initial pressure increase being thus experienced. The autoclave is allowed to stand for 8 hrs., at such temperature with stirring, whereafter it is allowed to cool to ambient temperature. The pressure is released and on the solution as obtained upon decantation, the gaschromatographic analysis indicates an 87% conversion of benzene to cyclohexane.

By adding to this catalytic mixture 300 mls of benzene and working under the same conditions as to temperature, hydrogen pressure and reaction time as before, a 79% conversion of benzene to cyclohexane is experienced.

I claim:

1. A method for hydrogenating aromatic unsaturated compounds characterized in that an aromatic unsaturated compound is caused to react with a catalyst system composed by:
    (a) A metal selected from the group consisting of the metals of the Groups IIA and IIIA of the Periodic System,
    (b) a primary or a secondary amine,
    (c) a halide selected from the group consisting of the halides of cobalt and nickel, and
    (d) an activator.
2. A method according to claim 1, characterized in that the metal is Mg or Al.

3. A method according to claim 1, characterized in that the amine is a member selected from the group consisting of methylamine, ethylamine, nor.propylamine, nor.butylamine, isopropylamine, sec.butylamine, tert.butylamine, cyclohexylamine, dimethylamine, diethylamine, di-isopropylamine.

4. A method according to claim 1, characterized in that the halide of Co or of Ni is $CoCl_2$, or $NiCl_2$, respectively.

5. A method according to claim 1, characterized in that the activating substance is a member selected from the group consisting of Na, NaH, $NaAlH_4$, $AlEt_3$, AND $MgEt_2$.

6. A method according to claim 1 characterized in that the molar ratio of the component (a) to component (b) of the catalytic system is nearly 1.

7. A method according to claim 1, characterized in that the molar ratio of the component (a) to the component (c) of the catalytic system varies between 0.1 and 100.

8. A method according to claim 1, characterized in that the molar ratio of the component (d) to component (a) of the catalytic system is near 0.5.

9. A method according to claim 1, characterized in that the molar ratio of the component (c) of the catalytic system to the substrate to be hydrogenated can exceed $1:10^6$.

10. A method according to claim 4, characterized in that the hydrogenation is carried out at a temperature comprised between the ambient temperature and the decomposition temperature of the product concerned.

11. A method according to claim 10, characterized in that the hydrogenation is carried out under a pressure comprised between atmospheric pressure and 1,000 atmospheres.

12. A method according to claim 11, characterized in that the substrate to be hydrogenated contains one or more aromatic rings.

13. A method according to claim 1, characterized in that the hydrogenation takes place during the reaction during which the catalyst is synthesized.

14. A method according to claim 1, characterized in that the hydrogenation is carried out by using the catalyst system which has already been employed in preceding hydrogenation runs.

15. A method according to claim 7, characterized in that the molar ratio of the component (a) to the component (c) of the catalytic system is from 4 to 8.

16. A method according to claim 8, characterized in that the molar ratio of the component (d) to the component (a) of the catalytic system is below 0.05.

17. A method according to claim 9, characterized in that the molar ratio of the component (c) of the catalytic system to the substrate to be hydrogenated is varied between $1:10^3$ and $1:10^4$.

18. A method according to claim 10, characterized in that the hydrogenation is carried out at a temperature comprised between 100° C. and 200° C.

19. A method according to claim 11, characterized in that the hydrogenation is carried out under a pressure comprised between atmospheric pressure and 150 atmospheres.

* * * * *